United States Patent
Lee

(10) Patent No.: US 9,970,953 B2
(45) Date of Patent: May 15, 2018

(54) MACHINE FOR AUTOMATED EXTRACTION OF NUCLEIC ACID

(71) Applicant: AccuBioMed Co., Ltd, New Taipei (TW)

(72) Inventor: Te Cheng Lee, New Taipei (TW)

(*) Notice: Subject to any disclaimer, the term of this patent is extended or adjusted under 35 U.S.C. 154(b) by 0 days. days.

(21) Appl. No.: 15/279,452

(22) Filed: Sep. 29, 2016

(65) Prior Publication Data
US 2017/0089936 A1    Mar. 30, 2017

(30) Foreign Application Priority Data
Sep. 30, 2015   (CN) .......................... 2015 1 0639013

(51) Int. Cl.
| | | |
|---|---|---|
| *G01N 35/10* | (2006.01) | |
| *G01N 35/02* | (2006.01) | |
| *C12N 15/10* | (2006.01) | |
| *G01N 35/04* | (2006.01) | |

(52) U.S. Cl.
CPC .......... *G01N 35/04* (2013.01); *C12N 15/101* (2013.01); *C12N 15/1017* (2013.01); *G01N 35/026* (2013.01); *G01N 35/10* (2013.01); *G01N 2035/0418* (2013.01)

(58) Field of Classification Search
CPC .......... G01N 2035/0401; G01N 35/04; G01N 35/02; G01N 35/1083; G01N 35/0099; G01N 35/10; G01N 2035/0415; G01N 2035/0418; G01N 2035/0424; B01L 35/10; B01L 35/1002; B01L 35/1011
See application file for complete search history.

(56) References Cited

U.S. PATENT DOCUMENTS

| | | | | |
|---|---|---|---|---|
| 4,478,094 A | * | 10/1984 | Salomaa ................. | G01N 1/38 422/552 |
| 4,554,839 A | * | 11/1985 | Hewett ................. | B01L 3/5085 422/561 |
| 4,555,957 A | * | 12/1985 | Frankel .............. | G01N 35/1083 73/864.14 |
| 4,952,518 A | * | 8/1990 | Johnson ................ | B01L 3/5085 422/65 |
| 5,497,670 A | * | 3/1996 | Carl ........................ | B01L 9/543 73/863.32 |
| 6,133,045 A | * | 10/2000 | Johnson .............. | B01L 3/50255 210/406 |
| 6,374,683 B1 | * | 4/2002 | Hunicke-Smith ..... | B01L 3/0217 73/863.32 |
| 6,582,664 B2 | * | 6/2003 | Bevirt ................... | B01L 3/0227 422/501 |
| 6,627,446 B1 | * | 9/2003 | Roach .............. | G01N 27/44704 204/451 |
| 6,694,197 B1 | * | 2/2004 | Hatcher ............... | G01N 35/109 422/510 |
| 6,982,063 B2 | * | 1/2006 | Hamel ................. | G01N 35/028 422/511 |
| 7,858,041 B2 | * | 12/2010 | Muraishi ................. | B01L 3/021 422/511 |

(Continued)

*Primary Examiner* — Brian R Gordon

(57) ABSTRACT

The present invention provides a machine for automated extraction of nucleic acid, which includes: a machine bottom plate, a support frame, and a vertical movement unit. The machine of the present invention can extract large-volume samples for automated extraction of nucleic acid, and if so desired, the extracted nucleic acid can be concentrated to produce high-quality nucleic acid samples.

8 Claims, 7 Drawing Sheets

(56) References Cited

U.S. PATENT DOCUMENTS

| | | | | |
|---|---|---|---|---|
| 8,007,741 B1* | 8/2011 | Heyes | ............... | G01N 35/0099 422/500 |
| 8,034,304 B2* | 10/2011 | Karlsson | ............... | B01J 8/008 422/501 |
| 8,163,183 B2* | 4/2012 | Tajima | ............... | G01N 35/0098 210/222 |
| 8,685,342 B2* | 4/2014 | Steinbrenner | ............ | B01L 3/02 422/501 |
| 9,579,646 B2* | 2/2017 | Richardson | ............ | B01L 3/0279 |
| 2003/0215360 A1* | 11/2003 | Ruddock | ............... | B01L 3/0279 422/63 |
| 2011/0127292 A1* | 6/2011 | Sarofim | ............... | B01L 9/52 422/521 |
| 2011/0268628 A1* | 11/2011 | Warhurst | ............ | B01L 3/0234 422/511 |
| 2013/0017128 A1* | 1/2013 | Silbert | ............... | G01N 35/0099 422/509 |
| 2013/0068041 A1* | 3/2013 | Naumann | ............ | B01L 3/0217 73/864.01 |
| 2014/0004020 A1* | 1/2014 | Tubbs | ............... | B01L 9/54 422/509 |
| 2015/0251781 A1* | 9/2015 | Matsukuma | ............ | B65B 3/003 141/2 |
| 2017/0045542 A1* | 2/2017 | Lapham | ............... | G01N 35/026 |

* cited by examiner

MACHINE FOR AUTOMATED EXTRACTION OF NUCLEIC ACID

BACKGROUND

1. Technical Field

The present invention provides a machine for automated extraction of nucleic acid, especially a machine for automatic extracting nucleic acid from large-volume samples and thereby the volume of the samples can be concentrated.

2. Prior Art

With the development of biotechnology and the decoding of hereditary substances, more and more biology-related, or even forensic, labs and hospitals extract nucleic acid from specimens on a regular basis in order to conduct experiments or tests. Nucleic acid can be extracted and purified in many ways, the most common of which can be divided into the following three categories: column extraction, magnetic bead extraction, and reagent extraction, wherein reagent extraction can be further divided into organic solvent extraction and non-organic solvent extraction. While each extraction method has its pros and cons, column extraction is currently the safest and easiest in terms of operation and also the most effective.

The process flow of column extraction is briefly stated as follows. To start with, the treated specimen (e.g., treated with an anionic detergent in order to break cells, release nucleic acid therefrom, and denature protein) in a microcentrifuge tube is transferred to a purification tube, in which a purification membrane is provided and whose bottom end has a passageway through which a liquid can flow out of the tube. Generally, the specimen in the microcentrifuge tube is drawn out with a micropipette and injected into the purification tube from above. After that, the purification tube is inserted into a waste liquid tube, and the double-tube assembly is subjected to centrifugation in a centrifuge in order for the nucleic acid, which is negatively charged, to bind with and be adsorbed onto the purification membrane, which is positively charged. In the meantime, impurities are driven through the purification membrane by the centrifugal force and flow into the waste liquid tube through the passageway at the bottom end of the purification tube. The foregoing step is referred to as the "binding step". Next, the "cleaning step" is performed by adding a cleaning liquid into the purification tube and starting centrifugation again to remove any impurities on the purification membrane and thereby increase the purity of the nucleic acid to be obtained. Lastly, the purification tube together with the nucleic acid-loaded purification membrane is transferred into a collection tube, in which an eluent of a specific salinity and pH value is subsequently added to change the electrical properties of the purification membrane, and the nucleic acid is separated from the purification membrane by centrifuging once more, then flows out of the purification tube, and eventually gathers in the collection tube. The last step is known as the "collection step".

The column extraction method described above is rather complicated. While the market has been supplied with automated centrifugal column extraction machines, those machines are disadvantaged by a time-consuming extraction process and are unsuitable for extracting nucleic acid from large-volume samples because they must be equipped with a centrifuge and are subject to limitations imposed by the volume of the column

SUMMARY

To solve the above problems, the present invention provides a machine for automated extraction of nucleic acid, including: a machine bottom plate, a horizontal track, a tray fixing frame, a reagent tray, a reagent holding plate, a sample tray, a heating base, a supporting frame, a vertical movement unit, a base plate track, a moving block, a syringe fixing unit, and at least one syringe. The horizontal track is on top of the machine bottom plate. The tray fixing frame is on top of the machine bottom plate and the horizontal track. The reagent tray is in the tray fixing frame. The reagent holding plate is in the fixing frame. The sample tray is in the tray fixing frame. The heating base is in the tray fixing frame and under the reagent tray. The supporting frame is vertically on top of the machine bottom plate and including a vertical track on a lateral side of the supporting frame facing the tray fixing frame. The vertical movement unit is connected to the supporting frame and including a base plate and a vertical movement unit track, wherein the base plate can be vertically moved along the vertical movement unit track. The base plate track is on the base plate. The moving block is horizontally set to the base plate track and having a plunger fixing unit. The syringe fixing unit is under the moving block locked to the base plate and connected to the plunger fixing unit. The syringe includes a plunger and the plunger is mounted on the syringe fixing unit.

In one preferred embodiment of the present invention, the above machine further comprises: a material returning plate, a spring mechanism, and a motor. The material returning plate is under the syringe fixing unit. The spring mechanism is on two lateral sides of the syringe fixing unit and is controlled by a motor. The spring mechanism is configured to drive the material returning plate into vertical movement. The motor is on the base plate.

In one preferred embodiment of the present invention, the reagent tray includes a tray base and a tray cover. The tray base comprises at least one cartridge, at least one centrifuge tube receiving space, and at least one centrifuge cover receiving space; wherein, the cartridge receiving space is a long narrow rectangle-shaped groove arranged on the tray base, the centrifuge tube receiving space is a round hole, and the centrifuge tube cover receiving space is an oval-like notch; and, the centrifuge tube receiving space and the centrifuge tube cover receiving space are arranged in a staggered manner on one end of the cartridge receiving space. The tray cover is opened or closed with respect to the tray base and including at least one aperture, wherein this one aperture is corresponding to at least one the centrifuge tube receiving space.

In one preferred embodiment of the present invention, the above machine further comprises at least one cartridge in the cartridge receiving space. The cartridge includes: a pipette receiving space, a column cover receiving space, a nucleic acid binding column receiving space, an adapter pipette receiving space, at least two heated receiving space, and a plurality of receiving spaces, which are arranged in a sequential order. Further, the pipette receiving space, the nucleic acid binding column receiving space, the adapter pipette receiving space, the heated receiving space, and the receiving spaces are round holes and the column cover receiving space is a rectangle-shaped groove.

In one preferred embodiment of the present invention, the cartridge receiving space and the cartridge respectively comprise corresponding male and female engaging features; wherein the cartridge receiving space has a stop plate lying above a bottom end portion of the cartridge receiving space.

In one preferred embodiment of the present invention, the reagent holding plate is configured to receive a reagent container loaded with a binding liquid and an absorptive liquid container loaded with an absorptive liquid.

In one preferred embodiment of the present invention, the sample tray is configured to receive a sample container loaded with the sample on which extraction is to be performed.

In one preferred embodiment of the present invention, the tray fixing frame has a first end and a second end opposite to the first end, and the reagent tray, the reagent holding plate, and the sample tray are in the tray fixing frame in a sequential order from the first end to the second end.

In one preferred embodiment of the present invention, the syringe has a volume of 10~100 cc.

In one preferred embodiment of the present invention, the syringe comprises a lower end; wherein the lower end includes a first engaging structure and a second engaging structure below the first engaging structure.

The machines of the present invention has the following advantages over the prior art:

1. Nucleic acid can be extracted more efficiently by the machine for automated extraction of nucleic acid of the present invention than by the conventional manual column extraction method.

2. Nucleic acid can be extracted from large-volume samples by the machine for automated extraction of nucleic acid of the present invention, and if so desired, the extracted nucleic acid can be concentrated to produce high-quality nucleic acid samples.

3. The special arrangement of the machine for automated extraction of nucleic acid of the present invention allows the extraction process of each sample to take place in an individual cartridge without the risk of mutual interference or contamination.

4. The cartridge of the machine for automated extraction of nucleic acid of the present invention is integrally formed and can be discarded after use, and each liquid material used can be "drawn and discharged at the same position" by the machine of the present invention. More specifically, a liquid material can be discharged where it is previously drawn or into another desired container during the extraction process and therefore need not be collected by a special waste liquid container. When the cartridge of the present invention is used, all the waste liquids are back in their respective original positions in the cartridge upon completion of nucleic acid extraction, and the used cartridge can be directly discarded. Thus, the cartridge reduces the risk of cross-contamination and provides convenience of use.

BRIEF DESCRIPTION OF THE DRAWINGS

FIG. 3-1 schematically shows the reagent tray of the machine for automated extraction of nucleic acid of the present invention; FIG. 3-2 schematically shows the cartridge provided on the reagent tray of the machine for automated extraction of nucleic acid of the present invention.

FIG. 4-1 is front view of the machine for automated extraction of nucleic acid of the present invention; FIG. 4-2 shows the lateral view of the machine for automated extraction of nucleic acid of the present invention.

FIG. 5-1 shows the pipette of the present invention; FIG. 5-2 shows the nucleic acid binding column of the present invention; FIG. 5-3 shows the adapter pipette of the present invention; FIG. 5-4 shows the syringe of the present invention.

DETAILED DESCRIPTION

The terms "a", "an", "one" and "one kind" used herein mean the object phrase is one or more than one (at least one).

The following embodiments should not be regarded as unduly limiting the present invention. That the modification and exchanges of the following embodiments done by a person having ordinary skilled is without departing from the spirit or the scope of the present invention may still fall within the scope of the present invention. The whole structure and the manual process of the machine for automated extraction of nucleic acid of the present invention is described as following with drawings.

Embodiment 1

Figure 1:
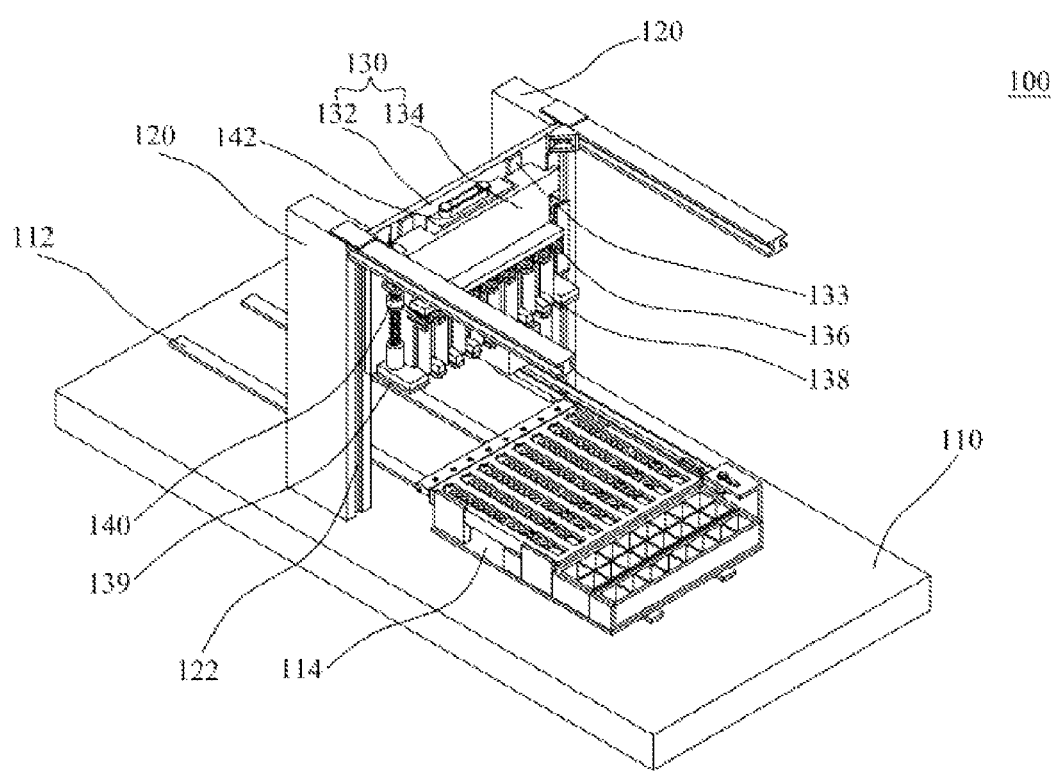
FIG. 1 schematically shows the machine of the present invention for automated extraction of nucleic acid.
Figure 2:
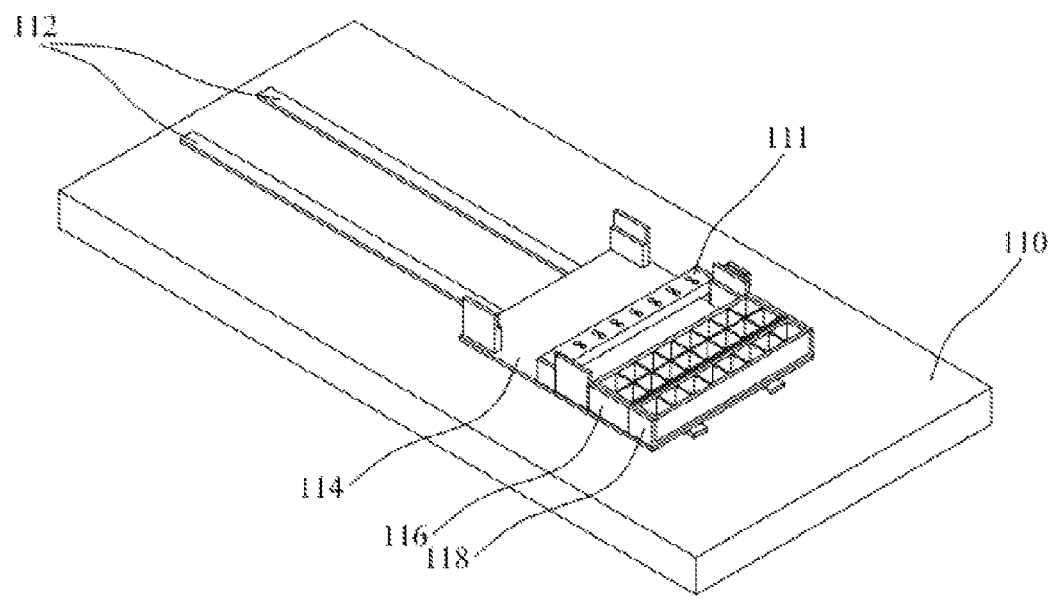
FIG. 2 schematically shows the base of the machine of the present invention for automated extraction of nucleic acid.
Figures 1, 3:
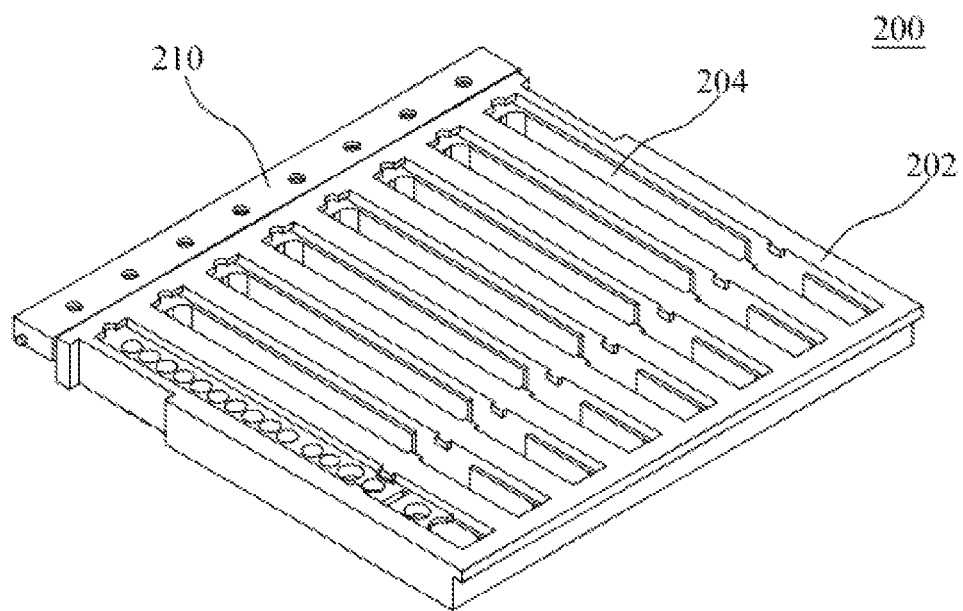
Figures 2, 3:
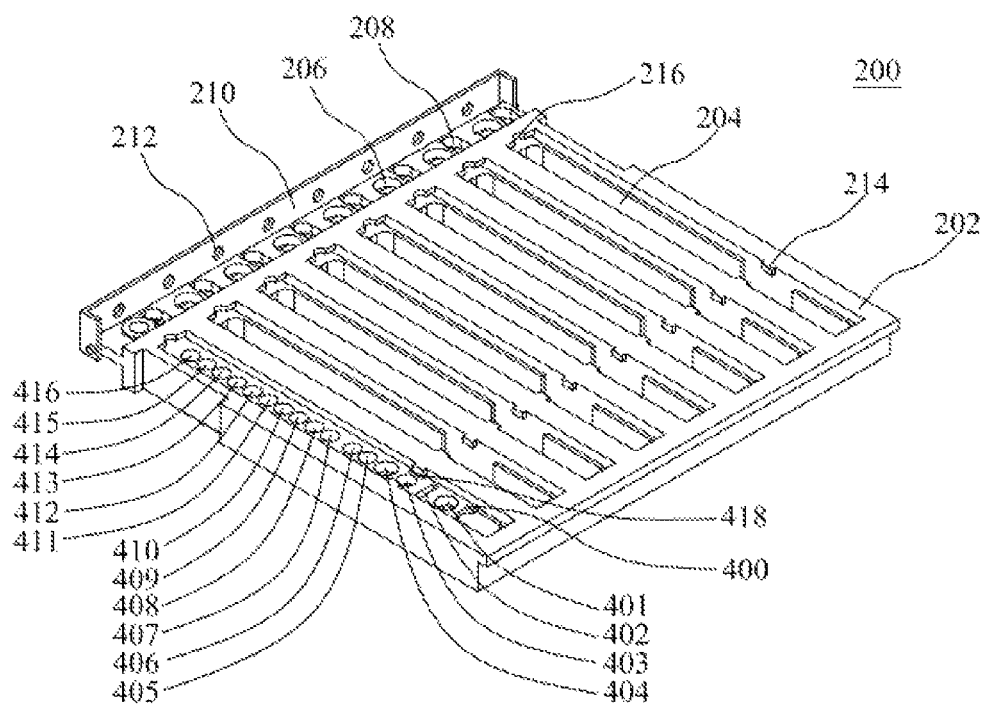

To begin with, please refer to FIG. 1 to FIG. 3, in which: FIG. 1 schematically shows the machine 100 of the present invention for automated extraction of nucleic acid, FIG. 2 schematically shows the base of the machine 100, and FIG. 3-1 and FIG. 3-2 schematically show the reagent tray 200 of the present invention. The machine 100 of the present invention includes a machine bottom plate 110, a supporting frame 120, and a vertical movement unit 130. The machine bottom plate 110 is provided with a horizontal track 112 and a tray fixing frame 114. The tray fixing frame 114 can be horizontally moved on the machine bottom plate 110 along the horizontal track 112. The tray fixing frame 114 is configured to receive a reagent tray 200, a reagent holding plate 116, and a sample tray 118 sequentially arranged in that order, wherein the reagent tray 200 has a tray cover 210 located on a side that faces away from the sample tray 118. In addition, the tray fixing frame 114 is provided with a heating base 111 while a heating device is provided under the sample tray 118. The supporting frame 120 is vertically provided on top of the machine bottom plate 110 and is provided with a vertical track 122. A vertical movement unit 130 is preferably plate-shaped and includes a base plate 132 and a vertical movement unit track (not shown) allowing the base plate 132 to move up and down with respect to the vertical movement unit 130. More specifically, the base plate 132 can be vertically moved along the vertical movement unit track. Also, a base plate track 133 is provided above the base plate 132, a moving block 134 is provided along the base plate track 133, and a syringe fixing unit 138 is provided under the moving block 134, locked to the base plate 132, and configured to be mounted with a syringe 300. The moving block 134 is provided with a plunger fixing unit 136 corresponding to the syringe 300 and configured to be mounted with a plunger 302 for the syringe 300 so that, when vertically moved along the base plate track 133, the moving block 134 drives the plunger 302 and thereby generates a positive or negative pressure in the syringe 300. Moreover, the base plate 132 is provided along the vertical track 122 and can drive the moving block 134 and the syringe fixing unit 138 into vertical movement with respect to the supporting frame 120.

Figures 1, 4:
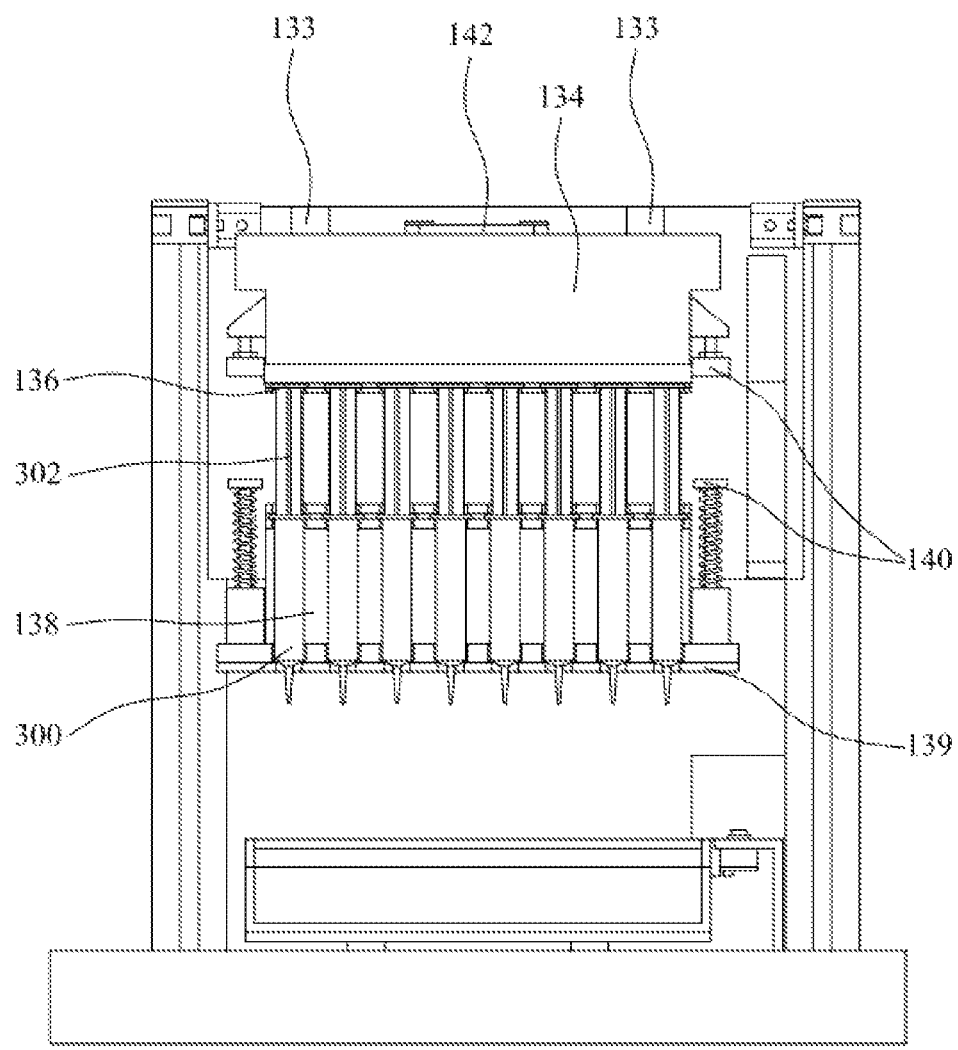
Figures 2, 4:
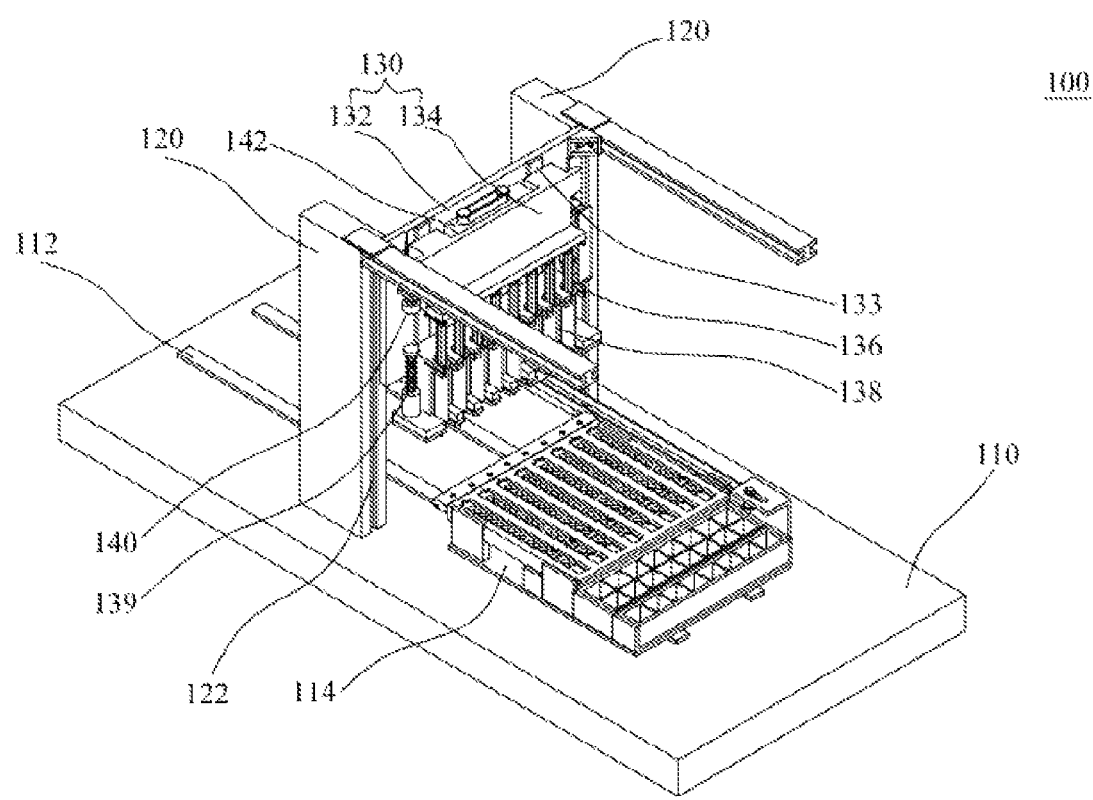

Referring to FIG. 4-1, which is a front view of the machine 100 of the present invention, a material returning plate 139 is provided under the syringe fixing unit 138, and a spring mechanism 140 is provided on two lateral sides of the syringe fixing unit 138 and is controlled by a motor 142.

The spring mechanism 140 is configured to drive the material returning plate 139 into vertical movement.

Referring back to FIG. 2, the reagent holding plate 116 is configured to receive a reagent container loaded with a binding liquid and an absorptive liquid container loaded with an absorptive liquid. The sample tray 118, on the other hand, is configured to receive a sample container loaded with the sample on which extraction is to be performed. The respective sizes of the absorptive liquid container, the reagent container, and the sample container can be designed according to user needs.

The structure of the reagent tray 200 is now detailed with reference to FIG. 3-1 and FIG. 3-2. The reagent tray 200 includes a tray base 202 as shown in FIG. 3-1, and the tray base 202 is provided with a cartridge receiving space 204, a centrifuge tube receiving space 206, and a centrifuge tube cover receiving space 208. A tray cover 210 is configured to be opened and closed with respect to the tray base 202 and, when closed, corresponds to and lies above the centrifuge tube receiving space 206 and the centrifuge tube cover receiving space 208. The tray cover 210 is provided with an aperture 212 corresponding in position to the centrifuge tube receiving space 206. Referring to FIG. 3-2 in conjunction with FIG. 5-1 to FIG. 5-3, the cartridge receiving space 204 of the reagent tray 200 is configured to receive a cartridge 400, wherein the cartridge 400 includes a pipette receiving space 401 for receiving a pipette 500, a nucleic acid binding column receiving space 403 for receiving a nucleic acid binding column 501, an adapter pipette receiving space 404 for receiving an adapter pipette 504, a heated receiving space 405, 406, and a plurality of receiving spaces 407~416. The receiving spaces 407~416 are preferably, but not necessarily, so configured that the receiving space 407 is to be loaded with a waste liquid, that each of the receiving spaces 408~415 is to receive a cleaning liquid, and that the receiving space 416 is to receive an eluent. The heating base 111 corresponds to and lies under the heated receiving space 405, 406. Preferably, the cartridge receiving space 204 is further provided with a column cover receiving space 402 beside the nucleic acid binding column receiving space 403 in order to receive the lid 502 of the nucleic acid binding column 501.

The cartridge receiving space 204 and the cartridge 400 are respectively provided with corresponding male and female engaging features 214 and 418. The cartridge receiving space 204 is further provided with a stop plate 216 corresponding to and lying above a bottom end portion of the cartridge receiving space 204, where the cartridge 400 is to be received. The cartridge 400 is placed into the cartridge receiving space 204 in such a way that the male and female engaging features 214 and 418 engage with each other. Then, the cartridge 400 is pushed toward the bottom end portion of the cartridge receiving space 204 until stopped by the stop plate 216 and thus secured in the cartridge receiving space 204. The male and female engaging features 214 and 418 form a foolproof device in order for the user to put the cartridge 400 into the cartridge receiving space 204 in the correct direction defined by the male and female engaging features 214 and 418.

A detailed description of how to use the automated nucleic acid extraction machine 100 and of the design concept of each structure of the machine 100 is given below with reference to the accompanying drawings.

[Preparation]

The reagent tray 200 is at its initial position, where it will not collide with the vertical movement unit 130 above. The sample on which extraction is to be performed is manually loaded into a sample container, in which a lysis buffer is subsequently added to disintegrate the cells or tissues in the sample and thereby release nucleic acid from the cells or tissues. The sample container is then put on the sample tray 118, in order for the heating device under the sample tray 118 to heat the sample in the sample container to 30~100° C., preferably to 37, 56, or 90° C., and thus increase the amount of the nucleic acid released. Following that, a reagent container loaded with a binding liquid and an absorptive liquid container loaded with an absorptive liquid are placed on the reagent holding plate 116. Preferably, the sample container, the reagent (i.e., binding liquid) container, and the absorptive liquid container are placed in such an order that the sample container (which is the closest to the user) is put on the sample tray 118 first, and that the reagent container and the absorptive liquid container (which are farther from the user) are put on the reagent holding plate 116 later. Then, the cartridge 400 is mounted with the pipette 500, the nucleic acid binding column 501, and the adapter pipette 504 and is put into the cartridge receiving space 204 of the reagent tray 200, an empty centrifuge tube is put into the centrifuge tube receiving space 206, and the cover of the centrifuge tube is put into the centrifuge tube cover receiving space 208. The tray cover 210 is subsequently shut, and the reagent tray 200, loaded onto the machine 100. To complete the preparation, the syringe 300 and the plunger 302 are mounted on the syringe fixing unit 138 and the plunger fixing unit 136 respectively.

[Mixing Step]

The reagent tray 200 on the machine bottom plate 110 is driven by the tray fixing frame 114 along the horizontal track 112 to a position where the syringe 300 corresponds to the pipette 500. Afterward, the vertical movement unit 130 moves the base plate 132 downward to connect the pipette 500 to the syringe 300. The reagent tray 200 is then moved to a position where the syringe 300 corresponds to the sample container on the sample tray 118. The base plate 132 of the vertical movement unit 130 is moved downward again to bring the pipette 500 into contact with the sample in the sample container, and then the moving block 134 is moved up and down to push and pull the plunger 302, thereby creating in turn a positive pressure and a negative pressure in the syringe 300 to mix the sample in the sample container (as shown in FIG. 1, in which the moving block 134 is moved downward and drives the plunger 302 downward to create a positive pressure in the syringe 300 and thereby discharge any liquid in the syringe 300, and FIG. 4-2, in which the moving block 134 is moved upward and drives the plunger 302 upward to create a negative pressure in the syringe 300 and thereby draw a liquid into the syringe 300). Once mixing is completed, the syringe 300 is moved upward (hereinafter, all references to the syringe 300 as being moved upward or downward refer to the syringe 300 being driven upward or downward by the base plate 132 of the vertical movement unit 130 moving upward or downward along the vertical movement unit track with respect to the vertical movement unit 130), and the reagent tray 200 is moved to a position where the syringe 300 corresponds to the reagent container, which contains the binding liquid. Then, the syringe 300 is moved downward to draw the binding liquid (hereinafter, all references to the syringe 300 as drawing, discharging, or mixing a liquid refer to the syringe 300 creating a positive pressure and/or a negative pressure in response to the plunger 302 being pushed and/or pulled by vertical movement of the moving block 134, thereby drawing a liquid, discharging a liquid, or repeating the drawing and discharging actions to mix a liquid). The syringe 300 is subsequently moved upward, and the reagent tray 200 is moved once again to the position where the syringe 300 corresponds to the sample container on the sample tray 118. Then, the syringe 300 is moved downward to discharge the binding liquid into the sample container and mix the liquid in the sample container. When mixing is completed, the reagent tray 200 is moved to the position where the syringe 300 corresponds to the pipette receiving space 401 (i.e., where the pipette 500 is connected to the syringe 300 at an earlier time), and the spring mechanism 140 drives the material returning plate 139 downward under the control of the motor 142 in order to return the pipette 500 on the syringe 300 to the pipette receiving space 401. Once the pipette 500 is back in place, the syringe 300 is moved upward to conclude the mixing step.

[Binding Step]

The reagent tray 200 is moved to a position where the syringe 300 corresponds to the nucleic acid binding column 501. Then, the syringe 300 is moved downward to connect with the nucleic acid binding column 501. After that, the syringe 300 is moved upward, and the reagent tray 200 is moved to a position where the syringe 300 corresponds to the adapter pipette 504. The syringe 300 is moved downward again to connect with the adapter pipette 504 and is then moved upward, and the reagent tray 200 is moved to the position where the syringe 300 corresponds to the sample container. The syringe 300 is subsequently moved downward to draw all the sample in the sample container. Then, the syringe 300 is moved upward, and the reagent tray 200 is moved to a position where the syringe 300 corresponds to the absorptive liquid container, which is loaded with the absorptive liquid. The syringe 300 is then moved downward to discharge its liquid content into the absorptive liquid container. As the nucleic acid binding column 501 has a purification membrane 503, and the nuclide acid in the sample has now bound to the purification membrane 503, the liquid discharged from the syringe 300 into the absorptive liquid container is a waste liquid. The discharge of the waste liquid, however, tends to generate a large amount of bubbles due to the fact that the lysis buffer containing the nucleic acid of the specimen also contains a large amount of surfactant. The bubbles, if present, may hinder operation or even flow out of the container to cause contamination. In consideration of this, the absorptive liquid has a bubble absorbing ingredient (e.g., a defoaming agent). When the waste liquid is discharged into the absorptive liquid container, therefore, bubbles resulting from a mixture of liquid and air will be absorbed by the mixed liquid and kept from flowing out of the absorptive liquid container, thus reducing the risk of contamination. The binding step is completed by moving the syringe 300 upward.

[Cleaning Step]

The reagent tray 200 is moved to a position where the syringe 300 corresponds to the receiving space 408, which is loaded with a cleaning liquid. The syringe 300 is then moved downward to draw the cleaning liquid, in order for the cleaning liquid to pass through and thereby clean the purification membrane 503 in the nucleic acid binding column 501. Following that, the syringe 300 is moved upward, and the reagent tray 200 is moved to a position where the syringe 300 corresponds to the receiving space 407. The syringe 300 is subsequently moved downward to discharge the waste liquid into the receiving space 407. It should be pointed out that the cleaning operation can be repeated several times. More specifically, the reagent tray 200 can be further moved to a position where the syringe 300 corresponds to the receiving space 409, which is loaded with a cleaning liquid, and the waste liquid generated by cleaning the purification membrane 503 is discharged into the previous receiving space 408, from which the cleaning liquid has been drawn for the previous cleaning cycle. The following cleaning cycles can be carried out in a similar manner. The cleaning step is completed by moving the syringe 300 upward.

[Air-Drying Step]

The reagent tray 200 is moved to a position where the syringe 300 corresponds to the heated receiving space 405, under which a heating base 111 is provided. The heating base 111 is configured for heating at 30 to 100° C., preferably 50 to 70° C., and more preferably 65° C. The syringe 300 is moved downward such that the nucleic acid binding column 501 and the adapter pipette 504, both connected to the syringe 300, are received in the heated receiving space 405. The cleaning liquid remaining on the purification membrane 503 is dried, and the alcohol left from the cleaning liquid, evaporated, by heating through air in order to make subsequent nucleic acid collection more efficient. Preferably, the heating base 111 is activated during the third cleaning cycle of the previous cleaning step, for the reagents in the cartridge 400 may deteriorate if the heating base 111 has been in operation for too long. The air-drying step is concluded by moving the syringe 300 upward.

[Collection Step]

The reagent tray 200 is moved to a position where the syringe 300 corresponds to the receiving space 416, where an eluent is received. Then, the syringe 300 is moved downward to draw the eluent, in order for the eluent to pass through the purification membrane 503 in the nucleic acid binding column 501 and thereby release the adsorbed nucleic acid into the eluent. After that, the syringe 300 is moved upward, and the reagent tray 200 is moved to a position where the syringe 300 corresponds to the centrifuge tube receiving space 206, where a centrifuge tube is received. The syringe 300 is then moved downward and discharges the nucleic acid-containing eluent through the aperture 212 of the tray cover 210 into the centrifuge tube in the centrifuge tube receiving space 206. Thanks to the height difference provided by the tray cover 210, the front end of the adapter pipette 504 on the syringe 300 will not touch the bottom of the centrifuge tube, and this prevents the nucleic acid-containing eluent from splashing, which may otherwise occur due to the pressure generated by pressing the front end of the adapter pipette 504 against the bottom of the centrifuge tube when the eluent is discharged into the centrifuge tube. The syringe 300 is subsequently moved upward to complete the collection step.

[Recycling Step]

The reagent tray 200 is moved to the position where the syringe 300 corresponds to the adapter pipette receiving space 404. Then, the spring mechanism 140 drives the material returning plate 139 downward under the control of the motor 142 in order to bring the adapter pipette 504 on the syringe 300 back into the adapter pipette receiving space 404. Following that, the reagent tray 200 is moved to the position where the syringe 300 corresponds to the nucleic acid binding column receiving space 403, and the spring mechanism 140 once again drives the material returning plate 139 downward under the control of the motor 142 in order to bring the nucleic acid binding column 501 on the syringe 300 back into the nucleic acid binding column receiving space 403. The reagent tray 200 is subsequently returned to its initial position, allowing the user to remove the entire reagent tray 200 from the machine 100, open the tray cover 201, and take out the centrifuge tube, where the nucleic acid-containing eluent is collected. The used cartridge 400 can then be removed and discarded.

If the nucleic acid to be extracted from a sample is DNA, the binding step can be modified as follows: after the syringe 300 is moved downward to connect with the adapter pipette 504, the eluent is drawn into the heated receiving space 406 of the cartridge 400 first, and the sample is drawn at a later time in order for the nucleic acid in the sample to bind to the purification membrane 503. In that case, the subsequent cleaning step remains the same whereas the collection step must be modified correspondingly such that the syringe 300 is moved not to the receiving space 416 to draw the eluent once received therein, but to the heated receiving space 406 to draw the heated eluent, whose temperature is about 30~100° C., preferably 50~70° C., and more preferably 65° C. By passing the heated eluent through the purification membrane 503 in the nucleic acid binding column 501, the release of nucleic acid into the eluent and consequently the collection of DNA are rendered more efficient.

Embodiment 2

In another embodiment of the present invention, referring to FIG. 1, the supporting frame 120 can also be horizontally moved. In other words, the machine bottom plate 110 can be provided with another horizontal track (not shown) corresponding to and lying under the supporting frame 120, in order for the supporting frame 120 to move horizontally along with the vertical movement unit 130 provided thereon. Therefore, the second embodiment is different from the first embodiment in that, while the machine 100 performs automated nucleic acid extraction, it is not necessarily the case that the reagent tray 200 is driven into horizontal movement along the horizontal track 112 by the tray fixing frame 114; rather, the supporting frame 120 can be horizontally moved to bring the syringe 300 to the positions in each step of the first embodiment.

Embodiment 3

Figures 1, 5:
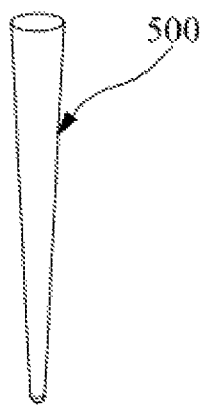
Figures 2, 5:
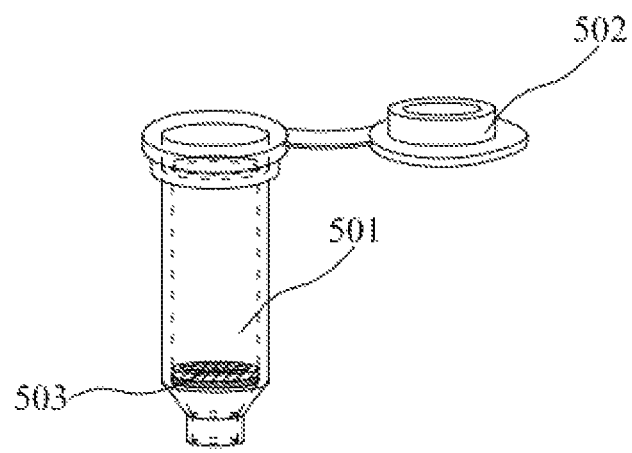
Figures 3, 5:
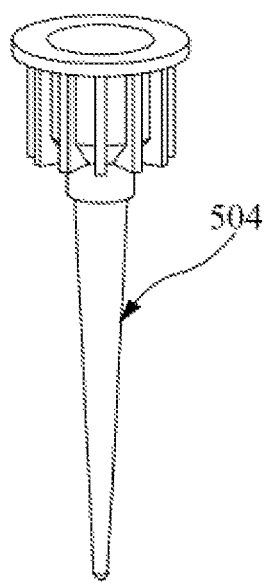
Figures 4, 5:
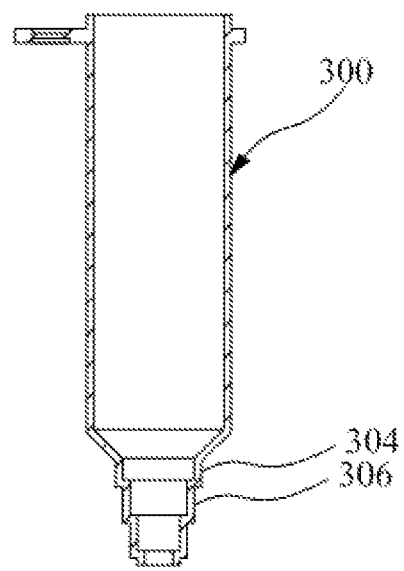

Yet another embodiment of the present invention provides the syringe 300 for use in the foregoing machine 100 for automated extraction of nucleic acid. Referring to FIG. 5-4, the front end of the syringe 300 has an upper engaging feature 304 and a lower engaging feature 306. The upper engaging feature 304 and the lower engaging feature 306 do not have to be of any particular shapes, provided that they can be detachably mounted with the pipette 500 in FIG. 5-1 and the nucleic acid binding column 501 in FIG. 5-2. In a preferred embodiment, the upper engaging feature 304 is configured for detachable engagement with the pipette 500, and the lower engaging feature 306, with the nucleic acid binding column 501.

When the machine 100 of the present invention and corresponding devices are used, each liquid material employed can be "drawn and discharged at the same position". That is to say, any liquid material used in the extraction process can be discharged to where it is previously drawn or to any other container if so desired. Moreover, all the containers required are arranged in a row, which defines the moving path of the syringe 300, and there is no need to collect the waste liquids with special waste liquid containers because all the waste liquids will return to their original positions in the cartridge 400 respectively. In addition, the used purification cartridge can be directly discarded, thus not only providing convenience of use but also reducing the risk of cross-contamination.

Furthermore, as the syringe 300 is configured to draw a large-volume sample (e.g., the syringe 300 has a volume of 10~100 cc), the machine 100 of the present invention can extract nucleic acid from a large-volume sample in an automated manner, allowing the nucleic acid in the sample to bind to the purification membrane 503, but draw only a small-volume (e.g., about 200 µl) eluent with the syringe 300 in the collection step in order to concentrate the eluted nucleic acid and thereby produce a high-quality nucleic acid extract.

What is claimed is:
1. A machine (100) for automated extraction of nucleic acid, comprising:
   a machine bottom plate (110);
   a horizontal track (112), on top of the machine bottom plate (110);
   a tray fixing frame (114), on top of the machine bottom plate (110) and the horizontal track (112);
   a reagent tray (200), in the tray fixing frame (114);
   a reagent holding plate (116), in the tray fixing frame (114);
   a sample tray (118), in the tray fixing frame (114);
   a heating base (111), in the tray fixing frame (114) and under the reagent tray (200);
   a supporting frame (120), vertically on top of the machine bottom plate (110) and including a vertical track (122) on a lateral side of the supporting frame (120) facing the tray fixing frame (114);
   a vertical movement unit (130), connected to the supporting frame (120) and including a base plate (132) and a vertical movement unit track, wherein the base plate (132) can be vertically moved along the vertical movement unit track;
   a base plate track (133), on the base plate (132);
   a moving block (134), horizontally set to the base plate track (133) and having a plunger fixing unit (136);
   a syringe fixing unit (138), under the moving block (134), locked to the base plate (132) and connected to the plunger fixing unit (136); and,
   at least one syringe (300), including a plunger (302) and the plunger (302) mounted on the syringe fixing unit (138).
2. The machine (100) of claim 1, further comprising:
   a material returning plate (139), under the syringe fixing unit (138);
   a spring mechanism (140), on two lateral sides of the syringe fixing unit (138); and,
   a motor (142), on the base plate (132).
3. The machine (100) of claim 1, wherein the reagent tray (200) further comprises:
   a tray base (202), having at least one cartridge receiving space (204), at least one centrifuge tube receiving space (206), and at least one centrifuge tube cover receiving space (208), wherein the cartridge receiving space (204) is a rectangular-shaped groove arranged on the tray base, and the centrifuge tube receiving space (206) is a round hole and the centrifuge tube cover receiving space (208) is an oval-like notch, and the centrifuge tube receiving space (206) and the centrifuge tube cover receiving space (208) are arranged in a staggered manner on one end of the cartridge receiving space (204); and
   a tray cover (210), being opened or closed with respect to the tray base (202) and including at least one aperture (212), wherein this one aperture (212) is corresponding to at least one the centrifuge tube receiving space (206).

4. The machine (100) of claim 3, further comprising at least one cartridge (400) in the cartridge receiving space (204); the cartridge (400) includes:
 a pipette receiving space (401),
 a column cover receiving space (402),
 a nucleic acid binding column receiving space (403),
 an adapter pipette receiving space (404),
 at least two heated receiving spaces (405, 406), and
 a plurality of receiving spaces (407~416) arranged in a sequential order; wherein the pipette receiving space (401), the nucleic acid binding column receiving space (403), the adapter pipette receiving space (404), the heated receiving space (405, 406), and the receiving spaces (407~416) are round holes and the column cover receiving space (402) is a rectangular-shaped groove.

5. The machine (100) of claim 4, wherein the cartridge receiving space (204) and the cartridge (400) respectively comprise corresponding male and female engaging features (214) and (418); wherein the cartridge receiving space (204) has a stop plate (216) lying above a bottom end portion of the cartridge receiving space (204).

6. The machine (100) of claim 5, wherein the tray fixing frame (114) has a first end and a second end opposite to the first end, and the reagent tray (200), the reagent holding plate (116), and the sample tray (118) are in the tray fixing frame (114) in a sequential order from the first end to the second end.

7. The machine (100) of claim 1, wherein the syringe (300) has a volume of 10~100 cc.

8. The machine (100) of claim 1, wherein the syringe comprises a lower end that includes:
 a first engaging structure (304); and
 a second engaging structure (306) below the first engaging structure (304).

* * * * *